United States Patent
Owen et al.

(10) Patent No.: US 8,675,190 B2
(45) Date of Patent: Mar. 18, 2014

(54) LARGE-COLLECTION-AREA RAMAN PROBE WITH REDUCED BACKGROUND FLUORESCENCE

(75) Inventors: Harry Owen, Ann Arbor, MI (US); Kevin L. Davis, Ann Arbor, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 109 days.

(21) Appl. No.: 13/117,485

(22) Filed: May 27, 2011

(65) Prior Publication Data

US 2012/0300201 A1   Nov. 29, 2012

(51) Int. Cl.
*G01J 3/44* (2006.01)

(52) U.S. Cl.
USPC .......................................... 356/301

(58) Field of Classification Search
USPC ............................. 356/301, 72–73
See application file for complete search history.

(56) References Cited

U.S. PATENT DOCUMENTS

| | | |
|---|---|---|
| 4,573,761 A | 3/1986 | McLachlan et al. |
| 5,112,127 A | 5/1992 | Carrabba et al. |
| 5,842,995 A | 12/1998 | Mahadevan-Jansen et al. |
| 6,483,581 B1 | 11/2002 | Ben-Amotz et al. |
| 6,486,948 B1 | 11/2002 | Zeng |
| 6,795,177 B2 | 9/2004 | Doyle |
| 6,809,812 B2 | 10/2004 | Yin |
| 6,809,813 B2 | 10/2004 | Bennett et al. |
| 7,148,963 B2 | 12/2006 | Owen et al. |
| 2004/0152992 A1* | 8/2004 | Zeng ........................... 600/476 |

OTHER PUBLICATIONS

Huang, Z. et al., Rapid near-infrared Raman spectroscopy system for real-time in vivo skin measurements, Optic Letters, 26(22): 1782-1784, Nov. 15, 2001.
Smith, E. et al., Modern Raman Spectroscopy—A Practical Approach, Chap. 1, pp. 4-5, 2005.

* cited by examiner

*Primary Examiner* — Tarifur Chowdhury
*Assistant Examiner* — Abdullahi Nur
(74) *Attorney, Agent, or Firm* — Gifford, Krass, Sprinkle, Anderson & Citkowski, P.C.

(57) ABSTRACT

A compact Raman analysis system combines a near-infrared (NIR) laser source, a 2D array collecting anti-Stokes Raman spectra, and a probe configured to measure complex solid samples, including pharmaceutical tablets and other large-area targets with reduced background fluorescence at relatively low cost. The system collects spectra from an area of 1-mm or greater, preferably 3-12 mm or more, facilitating the collection of statistically useful data from inhomogeneous and laser-sensitive samples, among other applications. Potential pharmaceutical applications include tablet dosage level measurements, as well as online and at-line quality-control (QC) monitoring opportunities. Other applications include tablet identification as a forensic tool to identify counterfeit pharmaceutical products; granulation and blend uniformity for improved formulation via better process understanding.

25 Claims, 1 Drawing Sheet

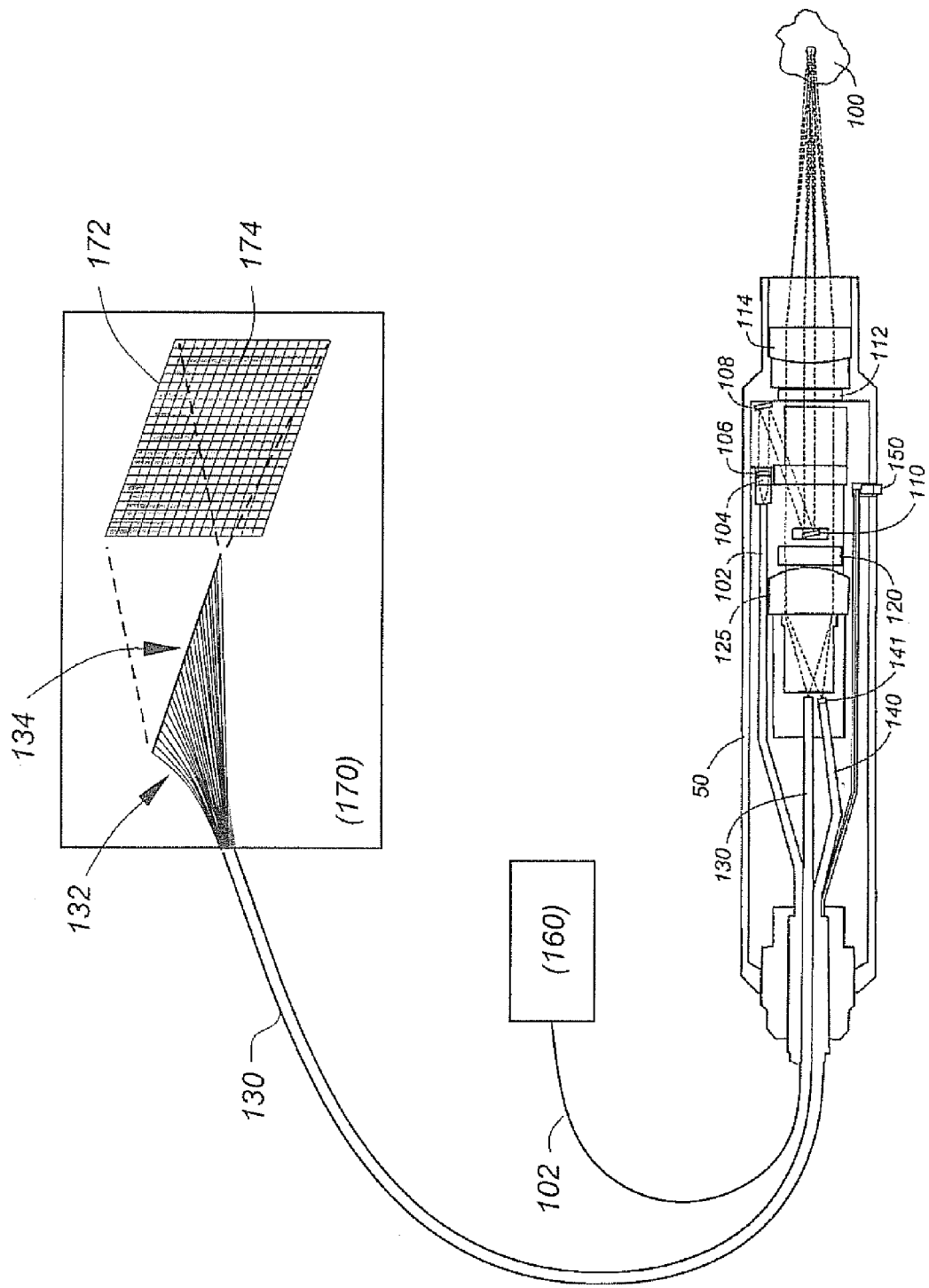

LARGE-COLLECTION-AREA RAMAN PROBE WITH REDUCED BACKGROUND FLUORESCENCE

FIELD OF THE INVENTION

This invention relates generally to optical measurement probes and, in particular, to a Raman probe having a large spot size with reduced background fluorescence.

BACKGROUND OF THE INVENTION

Fiber-optic probes make it possible to collect optical information such as Raman spectra without having to place the material being characterized inside a spectrometer housing. Such probes therefore simplify the interfacing of spectroscopic systems to samples under investigation, and allow analytical instruments to be located remotely from environments in need of spectroscopic monitoring.

The first remote fiber optic probes for Raman spectroscopy were reported by the McCreery group in the early 1980's. Their design used a single optical fiber to deliver laser light to the sample and a single optical fiber to collect light scattered by the sample. More specifically, divergent laser light from the laser delivery fiber was used to illuminate the sample, and light scattered from the sample within the acceptance cone of the collection fiber was transmitted back to the spectrograph. The efficiency of exciting and collecting Raman photons from any individual point in the sample was poor, but the integrated Raman intensity over the unusually large analysis volume compared favorably with the more traditional imaged illumination and collection configurations.

Several improvements to the McCreery Raman probe have more recently been reported. Instead of using just one collection fiber, multiple fibers have been used to increase the collection efficiency. For example, 6 fibers, each having the same diameter as the excitation fiber, may be grouped around the excitation fiber to form a single circular layer, as shown in U.S. Pat. No. 4,573,761. The performance of the McCreery type probe can also be modified for improved collection efficiency and/or working distance by changing the overlap between the emission cone of the excitation fiber and the collection cones of the collection fibers. An early realization of this idea, as disclosed in U.S. Pat. No. 4,573,761, angled the collection fibers such that their optic axes intersected the optic axis of the illumination fiber. This increased the overlap of the excitation and collection cones close to the tip of the fiber probe, where the excitation and collection of Raman photons was most efficient.

One further variation of the McCreery probe design is to use collection fibers having a different diameter than the excitation fiber. This additional variable is useful for changing the working distance of the probe and the fiber coupling to the spectrograph. However, one disadvantage of existing probes in their relatively small spot size. The large intensity of the small spot limits applications, often requiring scanning to cover a larger sample area. The high intensity of the small spot also precludes certain temperature-sensitive applications, including direct human contact. One of the most significant limitations of existing bundle probe designs is that they are not confocal, there is not complete overlap of the excitation light with the collection aperture.

Commonly assigned U.S. Pat. No. 7,148,963 describes a compact Raman/fluorescence confocal probe which is capable of collecting spectra from an area of 1 mm or greater, preferably 3-12 mm or more, as compared to current instruments which utilize spot sizes on the order of 2-60 microns. The fact that the large data collection area is confocal with the excitation light vastly improves the signal efficiency of the overall probe.

The larger spot size facilitates the collection of statistically useful data from inhomogeneous and laser-sensitive samples, among other applications. Potential pharmaceutical tablet applications include dosage level measurements, confirmation of desired polymorphic form, identification of unwanted polymorphic and amorphous forms of the active ingredient, as well as online and at-line quality-control (QC) monitoring opportunities. Other applications include tablet identification as a forensic tool to identify counterfeit pharmaceutical products; granulation and blend uniformity, tablet coating uniformity and active content within the coating for improved formulation via better process understanding Another area of interest is using the lower laser energy density provided by expanding the laser to up to 10 mm or more to analyze skin and the effects of cosmetics on skin without causing damage to the skin. The probe conforms to the ANSI standards and is therefore skin safe.

Previously implemented systems developed and demonstrated by Kaiser Optical Systems, Inc. use diode lasers (i.e., 785 nm, 830 nm) and large array CCD detectors (i.e., 1024 pixels by 256 pixels) allowing Raman spectra (Stokes shifted) to be collected in both reflectance and transmission of sufficient volume of sample to be representative of the whole sample. While the use of a large-area CCD provides distinct advantages, in some applications the excitation wavelengths generate sufficient fluorescence to limit the detection of low concentrations of critical components.

To reduce fluorescence from certain natural solid components (i.e., micro crystalline silica in pharmaceutical tablets) a near-infrared laser may be used in conjunction with an InGaAs detector combination to eliminate or reduce significantly fluorescence from natural materials such as Micro Crystalline Silica. The problem with such a configuration is that affordable InGaAs detectors are configured as a linear array, making them acceptable for moving liquid samples but not applicable to large area solid samples.

An outstanding need remains, therefore, for a Raman probe that collects spectra over a wide spot area while significantly reducing if not eliminating fluorescence from certain solid components.

SUMMARY OF THE INVENTION

This invention enables the measurement of complex solid samples, including pharmaceutical tablets and other targets with reduced background fluorescence at relatively low cost. To achieve this goal the preferred embodiments use a near-infrared (NIR) laser source, a 2D array collecting anti-Stokes Raman spectra, and a probe configured to produce a large spot size on the sample. This enables the system to measure low concentrations of critical components, including low-dosage, high-potency pharmaceutical samples.

A Raman analysis system constructed in accordance with the invention comprises a laser outputting a beam of excitation light having a nominal laser wavelength in the near-infrared (NIR) region of the spectrum. One or more excitation fibers carry the excitation light to a remote optical measurement probe, the probe including a plurality of optical elements which cooperate to facilitate the collection of Raman spectra over a sample spot confocal with the excitation light having a size on the order of 1 mm or greater. One or more collection fibers for carry the Raman spectra from the remote optical measurement probe to a spectrograph including a two-dimensional image sensor for receiving the Raman spectra generated on the anti-Stokes side of the laser wavelength. In the preferred embodiment, a single excitation fiber is used in conjunction with a bundle of collection fibers.

The system is capable of collecting spectra across a relatively large spot size, confocally as compared to traditional Raman probes. In the preferred embodiment, the remote probe collects spectra from an area of 1 mm or greater, preferably 3-12 mm or more, as compared to current instruments which utilize spot sizes on the order of 2-60 microns. The fact that the large data collection area is confocal with the excitation light vastly improves signal efficiency

BRIEF DESCRIPTION OF THE DRAWING

FIG. 1 is a simplified representation of an optical probe system constructed in accordance with this invention.

DETAILED DESCRIPTION OF THE INVENTION

Making reference to FIG. 1, a system constructed in accordance with this invention includes a laser source 160, spectrograph 170, and a remote optical measurement probe which may include various optical elements within housing 50 described in further detail below. Light from the laser 160 is delivered to the probe through excitation fiber(s) 102, and collected light for the sample is delivered to spectrograph 170 through collection fiber(s) 130.

Excitation light generated by laser source 160 produces a nominal wavelength in the near-infrared (NIR) region of the spectrum (i.e., in the 850 nm-1200 nm range). For example, due to the commercial availability of laser diode sources, a nominal laser wavelength of 993 nm may be used.

Although single and multiple fibers may be used for either the excitation or collection paths, in the preferred embodiment a single excitation fiber is used in conjunction with a bundle of collection fibers (typically 50, more or less). The diameter of the excitation fiber may vary, which dictates the ratio of the magnification of the excitation image to the collection image as discussed in further detail below. Excitation fibers in the range of 200 microns to 1 mm are preferred.

The collection fiber bundle preferably has an input end with the fibers arranged in a circle and an output end 132 with the fibers are arranged in a line 134 so that the resolution inherent in the use of small individual fibers is maintained at the spectrograph 170. In the preferred embodiment the spectrograph 170 uses a large array two-dimensional CCD image sensor 172 (i.e., 1024 by 256 pixels) to collect Raman spectra generated on the anti-Stokes side 174 of the laser wavelength. The inventive combination of a NIR source, a 2D array collecting anti-Stokes Raman spectra, and a probe configured to produce a large spot size enables the system to measure complex solid samples (pharmaceutical tablets, for example) with reduced background fluorescence at relatively low cost.

Continuing the reference to the FIGURE and now emphasizing the remote probe, excitation light from laser source delivered through fiber 102 is collimated by a short-focal-length lens 104 and passed through a bandpass filter 106 to remove fiber noise. From there the excitation light is reflected by a mirror 108 to a combiner 110, preferably a small wavelength-sensitive reflector (i.e., a reflective edge filter). The light then passes through an exit window 112, and is imaged by the sample lens 114 onto a sample 100.

Raman signal light and reflected, unshifted excitation light passes back through the sample lens 114 and through a notch filter 120. The combiner 110 occupies only a small amount of the return aperture, and thus has little effect on the collected light. The notch filter 120 removes the unshifted excitation light, leaving only the signal light to be focused onto the collection fiber(s) 130, which then connects to the spectrograph 170 for analysis. An optional indicator lamp may be provided as shown at 150. This is preferably electrically driven from a remote source to function as a cable breakage indicator as well.

To increase spot size, a pronounced asymmetric excitation-to-collection magnification ratio is used. In contrast to existing probe designs, wherein the ratio of the excitation image to the collection image at the target is less than 2:1 if not substantially the same, this invention utilizes a ratio of 2:1 or greater, up to 6:1 or higher in the preferred embodiments. To accomplish this, the focal length of the sample optic, which transmits a counter-propagating excitation/collection beam, is two to six times greater than the focal length of the excitation optic used to collimate the excitation beam, resulting in a highly magnified excitation image. In addition, the ratio of the focal length to the of the collection optic to the focal length of the excitation optic matches the ratio of the diameter of the excitation fiber(s) to the diameter of the collection fiber(s), so that the image diameters of the two fibers are approximately the same at the sample.

Since the focal length of the excitation lens 104 is small compared to that of the sample lens 114, the image of the excitation fiber is highly magnified. The focal length of the collection lens 125, however, is comparable to the sample lens 114 and is therefore less magnified. However, since the ratio of the collection and excitation lenses preferably matches the ratio of the diameter of the excitation fiber to the collection bundle diameter, the image diameters of the two fibers are approximately the same at the sample, optimizing signal-generation capacity.

The use of a collection fiber bundle is useful in various analysis situations, including uniformity measurements. For example, with respect to pharmaceutical applications, the signals across a group or all of the fibers may be measured to determine an average. While the average may be useful for certain information such as active ingredient dosage, individual or smaller groups of fibers may be sub-sampled to determine the distribution of constituents such as lubricants, fillers, binders, disintegrants, and other active or inactive ingredients. The uniformity of substances such as disintegrants is particularly useful, since an uneven distribution may affect dissolution as a function of time.

In order to function optimally, the fibers in the collection bundle may be calibrated. This is done through the use of a calibration fiber 140 carrying neon light or another calibration signal. This light illuminates a diffuser 141 disposed at the tip of fiber 140. Light from the diffuser 141 is collimated by the collection lens, which is partially reflected by the notch filter such that it forms an image of the diffuser on the collection fiber bundle.

The larger spot size facilitates the collection of statistically useful data from inhomogeneous and laser-sensitive samples, among other applications. Potential pharmaceutical applications include tablet dosage level measurements, as well as online and at-line quality-control (QC) monitoring opportunities. Other applications include tablet identification as a forensic tool to identify counterfeit pharmaceutical products; granulation and blend uniformity for improved formulation via better process understanding Another area of interest is using the lower laser energy density provided by expanding the laser to up to 10 mm or more to analyze skin and the effects of cosmetics on skin without causing damage to the skin. The probe conforms to the ANSI standards and is therefore skin safe.

We claim:

1. A Raman analysis system, comprising:
   a laser outputting a beam of excitation light having a nominal laser wavelength in the near-infrared (NIR) region of the spectrum;
   one or more excitation fibers for carrying the excitation light to a remote optical measurement probe, the probe including a plurality of optical elements which cooperate to facilitate the collection of Raman spectra over a sample spot confocal with the excitation light having a size on the order of 1 mm or greater; and
   one or more collection fibers for carrying the Raman spectra from the remote optical measurement probe to a spectrograph including a two-dimensional image sensor for receiving the Raman spectra generated on the anti-Stokes side of the laser wavelength.

2. The Raman analysis system of claim 1, wherein the optical elements within the probe include:
   an excitation lens for collimating the excitation light;
   a sample lens for focusing the excitation light onto the sample and for collimating light received from the sample; and
   wherein the focal length of the excitation lens is small compared to the focal length of the sample lens such that the image of the excitation fiber is highly magnified at the sample.

3. The Raman analysis system of claim 2, wherein the ratio of the focal length of the sample lens to the focal length of the excitation lens is 2:1 or greater.

4. The optical measurement probe of claim 1, further including:
   a bundle of collection fibers;
   an excitation lens for collimating the excitation light;
   a collection lens for focusing the Raman spectra onto the bundle of collection fibers; and
   wherein the ratio of the focal lengths of the collection and excitation lenses matches the ratio of the diameter of the excitation fiber to the collection bundle diameter such so that the image diameters of the two fibers are approximately the same at the sample.

5. The Raman analysis system of claim 1, further including:
   a bundle of collection fibers; and
   wherein the bundle has an input end with the fibers arranged in a circle and an output end with the fibers are arranged in a line.

6. The Raman analysis system of claim 1, further including:
   a sample lens for focusing the excitation light on to the sample and for collimating light received from the sample;
   a collection lens for focusing the Raman spectra onto the collection fiber, and wherein the focal length of the collection lens is comparable to the focal length of the sample lens.

7. The Raman analysis system of claim 1, including a single excitation fiber.

8. The Raman analysis system of claim 1, wherein the nominal laser wavelength is in the 830 nm-1200 nm range.

9. The Raman analysis system of claim 1, wherein the nominal laser wavelength is 993 nm.

10. A Raman analysis system, comprising:
    a laser outputting a beam of excitation light with a nominal laser wavelength in the near-infrared (NIR) region of the spectrum;
    one or more excitation fibers for carrying the excitation light to a sample under investigation through an optical measurement probe;
    an excitation lens within the probe for collimating the excitation light;
    a sample lens within the probe for focusing the excitation light onto the sample and for collimating light received from the sample;
    the focal length of the excitation lens being small compared to the focal length of the sample lens, such that the image of the excitation fiber is highly magnified at the sample, thereby facilitating the collection of Raman spectra from the sample over a spot size of 1 mm or greater; and
    one or more collection fibers for delivering the Raman spectra to a spectrograph including a two-dimensional image sensor for receiving the Raman spectra generated on the anti-Stokes side of the laser wavelength.

11. The Raman analysis system of claim 10, wherein the ratio of the focal length of the sample lens in the focal length of the excitation lens is 2:1 or greater.

12. The Raman analysis system of claim 10, further including:
    a bundle of collection fibers;
    a collection lens for focusing the Raman spectra onto the bundle of collection fibers; and
    wherein the ratio of the focal lengths of the collection and excitation lenses matches the ratio of the diameter of the excitation fiber to the collection bundle diameter such so that the image diameters of the two fibers are approximately the same at the sample.

13. The Raman analysis system of claim 12, wherein the bundle has an input end with the fibers arranged in a circle and an output end with the fibers are arranged in a line.

14. The Raman analysis system of claim 10, further including:
    a sample lens for focusing the excitation light on to the sample and for collimating light received from the sample;
    a collection lens for focusing the Raman spectra onto the collection fiber; and wherein the focal length or the collection lens is comparable to the focal length of the sample lens.

15. The Raman analysis system of claim 10, including a single excitation fiber.

16. The Raman analysis system of claim 10, wherein the nominal laser wavelength is in the 830 nm-1200 nm range.

17. The Raman analysis system of claim 10, wherein the nominal laser wavelength is 993 nm.

18. A Raman analysis system, comprising:
    a laser outputting a beam of excitation light having a nominal laser wavelength in the near-infrared (NIR) region of the spectrum;
    one or more excitation fibers for carrying excitation light to a sample under investigation;
    an excitation lens for collimating the excitation light;
    a bundle of collection fibers for delivering Raman spectra from the sample to a spectrograph including a two-dimensional image sensor for receiving the spectra on the anti-Stokes side of the laser wavelength;
    a collection lens for focusing the Raman spectra onto the bundle of collection fibers; and
    wherein the ratio of the collection and excitation lenses matches the ratio of the diameter of the excitation fiber to the collection bundle diameter such so that the image diameters of the two fibers are approximately the same at the sample, thereby facilitating the collection of the spectra over sample spot size of 1 mm or greater.

19. The Raman analysis system of claim 18, further including
   a sample lens for focusing the excitation light onto the sample and for collimating light received from the sample; and
   wherein the focal length of the excitation lens is small compared to the focal length of the sample lens such that the image of the excitation fiber is highly magnified at the sample.

20. The Raman analysis system of claim 18, wherein the ratio of the focal length of the sample lens to the focal length of the excitation lens is 2:1 or greater.

21. The Raman analysis system of claim 18, wherein the bundle has an input end with the fibers arranged in a circle and an output end with the fibers are arranged in a line.

22. The Raman analysis system of claim 18, further including:
   a sample lens for focusing the excitation light on to the sample and for collimating light received from the sample;
   a collection lens for focusing the Raman
   spectra onto the collection fiber; and wherein the focal length of the collection lens is comparable to the focal length of the sample lens.

23. The Raman analysis system of claim 18, further including a single excitation on fiber.

24. The Raman analysis system of claim 18, wherein the nominal laser wavelength is in the 830 nm-1200 nm range.

25. The Raman analysis system of claim 18, wherein the nominal laser wavelength is 993 nm.

* * * * *